United States Patent [19]

Zikán et al.

[11] 3,953,454

[45] Apr. 27, 1976

[54] N-(D-6-METHYL-8-ISOERGOLINE-I-YL)-N',N'-DIETHYLUREA

[75] Inventors: Viktor Zikán; Miroslav Semonský; Karel Řezábek; Miroslav Šeda; Marie Aušková, all of Prague, Czechoslovakia

[73] Assignee: SPOFA, United Pharmeceutical Works, Prague, Czechoslovakia

[22] Filed: Aug. 7, 1972

[21] Appl. No.: 278,367

[30] Foreign Application Priority Data
Aug. 5, 1971   Czechoslovakia .................. 5689-71
Aug. 5, 1971   Czechoslovakia .................. 5709-71

[52] U.S. Cl. ............................. 260/285.5; 424/261
[51] Int. Cl.² ...................................... C07D 457/06
[58] Field of Search ................................. 260/285.5

[56] References Cited
UNITED STATES PATENTS

| 3,113,133 | 12/1963 | Hofmann et al. | 260/285.5 |
| 3,251,846 | 5/1966 | Semonsky et al. | 260/285.5 |
| 3,270,020 | 8/1966 | Hofmann et al. | 260/285.5 |
| 3,324,133 | 6/1967 | Arlamone | 260/285.5 |
| 3,681,497 | 8/1972 | Semonsky et al. | 260/285.5 |

Primary Examiner—Donald G. Daus

[57] ABSTRACT

A new compound, N-(D-6-methyl-8-isoergoline-I-yl)-N', N'-diethylurea, processes for preparation and purification thereof, and therapeutic uses therefor in mammals.

3 Claims, No Drawings

N-(D-6-METHYL-8-ISOERGOLINE-I-YL)-N',N'-DIETHYLUREA

The invention relates to N-(D-6-methyl-8-isoergoline-I-yl)-N',N'-diethylurea of the formula

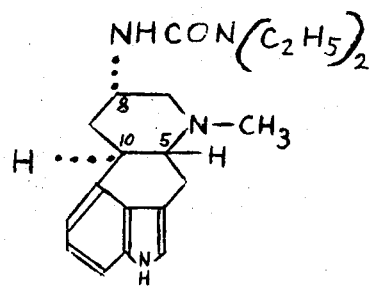

the salts thereof with organic and inorganic acids, as well as the process for producing them.

This new compound represents an analog of natural ergot alkaloids and because of the configuration at the assymmetrical centers, i.e. $C_{(5)}$, $C_{(8)}$ and $C_{(10)}$, it belongs in the group of D-dihydroisolysergic acid-I.

A pharmacological study of the new material brought out interesting properties which can be utilized in human as well as veterinary medicine.

Administration of said material orally, preferably in the form of its corresponding salts with organic or inorganic acids, prevents nidation with experimental animals and also exhibits at the same time an antilactation effect on, for example, rats, dogs, goats, pigs, which is caused by hindering of the endogenous secretion of prolactin.

During the experimental study for the aforedescribed effects, in the first instance, the compound was converted into an aqueous solution of the normal tartrate and was administered to a ten member group of adult female rats per os at 24 hour intervals, that is, five times in the first seven days after copulation. These animals were sacrificed on the 20th day and by means of sectioning the existence of the impregnation and eventually the condition of the embryos was controlled. A control group of the same size was administered under the same conditions only the solvent medium. As a medium effective dose (ED 50) an amount of about 50 µg was found with the normal tartrate of the compound.

During the checking of the antilactation effect with female rats an aqueous solution of the normal tartrate of the compound was administered per os to a group of seven nursing female rats, daily during four days, beginning on the 9th day after the birth of the litter. The milk production was, on the other hand, ascertained according to the daily weight increase of the nursing litter, and on the other hand, according to the filling of the stomach of the young with the milk (the milk was seen in the stomach region of the young as a visible white spot). The results were in both cases compared with results obtained with a control group of equal size. The dose which lowered the lactation to one-half (ED 50) amounted to about 120 µg/kg (according to the weight increase of the nursing young) and respectively about 85 µg/kg (according to the filling of the stomach of the young with milk).

The compound brought about, after the hindering of lactation with rats, estrus and the renewal of the estrous cycles. With female dogs it released the estrus, whereby their impregnation could be attained. This proves that this estrus is accompanied with a normal ovulation. With nursing female dogs this compound hindered the lactation, whereby there resulted in a few days a new estrus; with goats the lactation was lowered by a factor of four after a dose of 100 µ g(kg) per os was administered on two successive days.

The above results indicate that this material can be used in relatively broad range in veterinary medicine, for example, an auxiliary of treatment for the inflamation of milk glands with goats, cows and other animals. In the zoological technical practice this compound can, for example, be utilized for terminating lactation and for stimulating the bringing in heat of dogs and other animals, and eventually for the hindering of the impregnating of dogs after a racially undesirable pairing, and the like.

The new compound and its salts can be used in the aforementioned veterinary field either as described or in any suitable form of administration; they can be administered orally as well as parenterally.

According to the invention the new compound, N-(D-6-methyl-8-isoergoline-I-yl)-N/,N'diethylurea and its salts with organic or inorganic acids are manufactured by the following methods:

a. N-(D-6-methyl-8-isoergolenyl)-N'/,N'-diethylurea of the formula

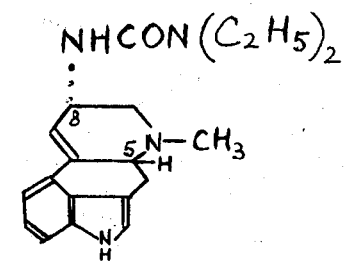

is catalytically hydrogenated in the presence of Raney-nickel as a catalyst, at a hydrogen pressure of 10 to 70 atm. and at a temperature of 35° to 90°C, in an inert organic solvent medium, preferably dioxane, whereby the crude product obtained is purified by means of column chromatography with simultaneous separation of the N-(D-6-methyl-8-isoergoline-II-yl)-N',N'-diethylurea which forms during hydrogenation and after eventual final purification by means of crystallization, the purified product is converted by neutralization with an organic or inorganic acid into the corresponding salt.

b. The D-dihydroisolysergic acid-I-azide is first of all converted to the D-6-methyl-8-isoergoline-I-ylisocyanate, which is reacted with diethylamine; thereafter the crude material obtained, after purification by means of column chromatography or/and crystallization, is converted by means of neutralization with an organic or inorganic acid into the corresponding salt.

The conversion of the D-dihydroisolysergicacid-I-azides into D-6-methyl-8-isoergoline-I-ylisocyanate can be carried out in an inert organic solvent medium, for example, in an aromatic hydrocarbon, preferably benzene, at the boiling temperature of the reaction mixture.

For reacting with D6-methyl-8-isoergoline-I-ylisocyanate it is advantageous that the diethylamine be used in a quantity of at least one molar equivalent.

If the reaction as set forth in paragraph(a) above is used then utilization of the Raney-nickel as catalyst in the hydrogenation of the material of the formula II is carried out for example in dioxane, at a hydrogen pressure of 35 atm. and at a temperature of 70°C; after taking up one molar equivalent of hydrogen for saturating the double bond in the 9,10-position and for forming a new assymmetrical center at $C_{(10)}$, there is formed both of the aforementioned isomers in a ratio relationship of 4 to 1. The utilization of palladium black as catalyst in the hydrogenation of the material of formula II, which is carried out in acetic acid with a hydrogen pressure of 35 atm. and a temperature of 20°C, gives a mixture of both isomers in a rather unfavorable ratio relationship of 2 to 3 and is also not suitable for the production of the desired compound. The isomer N-(D-6-methyl-8-isoergoline-II-yl)-N', N'-diethylurea, which belongs spatially in the group of D-dihydroisolysergic acid-II, is from the view point of antifertility, as well as anti-lactation effect, completely uninteresting and ineffective.

The separation of the crude reaction product, which is produced in a dry state after termination of the hydrogenation, followed by filtering out the catalyst and evaporating the filtrate is carried out advantageously by means of column-chromatography with aluminum oxide, for example by utilizing chloroform and its mixture with ethanol as the elution medium. The course of the column-chromatography can be followed by means of paper-chromatography with the use of the systems formamide-ammonium formate as stationary phase and of chloroform as a mobile phase. The column-chromatography furnishes the desired compound already in its very pure form; it can eventually be be finally purified by means of crystallization, for example from ethanol.

The operation as set forth in paragraph (b) above of the process in accordance with the invention represents a very advantageous possibility for obtaining the N-(D-6-methyl-8 -isoergoline-I-yl), N',N'-diethylurea. This process is carried out with available raw materials, the carrying out of the process is simple, and the single end product is obtained with high yields.

In carrying out the alternate process of the invention there is used as a starting material the D-dihydro-isolysergic acid-hydrazide (A. Stoll u. co-workers, Helv. Chim.Acta 29, 635, 1946), which is converted in a known manner into the base of the acid azide and is then used for the following reaction in the form of a dried solution in the used solvent medium.

By means of a brief boiling period of the solution, there is obtained the corresponding isocyanate, which is not isolated, but which is directly subjected to a further reaction with diethylamine. After terminating the reaction the volatile ingredients are removed by distillation under reduced pressure and the crude product is purified by means of column-chromatography with aluminum oxide. By working up the eluent there is already obtained a very pure material, which can eventually be finally purified by re-crystallization from a suitable solvent medium.

EXAMPLES

EXAMPLE 1

N-(D-6-methyl-8-isoergoline-I-yl)-N',N'-diethylurea (material I)

A solution of 1.9 g N-(D-6-methyl-8-isoergolenyl)-N',N'-diethylurea in 120 ml dioxane was hydrogenated in a rocking autoclave at a hydrogen pressure of 35 atm. and at a temperature of 70°C in the presence of 3.0 g Raneynickel until one molar equivalent of hydrogen had been taken up. After the termination of the hydrogenation, the catalyst was filtered off and the filtrate separated from the volatile ingredients by means of distillation under reduced pressure of a pump. The residue was taken up in chloroform; the chloroform solution was shaken with 1 M $NaHCo_3$, and with water, and after drying ($Na_2So_4$) the filtrate was evaporated to complete dryness under reduced pressure and dried at 40°C/2 Torr. 1.70 grams (90% of the theoretical amount) of a raw mixture of the material I was obtained with the isomer isoergoline-II-yl compound in a ratio of 4:1 . This basic mixture was dissolved in chloroform and the solution chromatograhed in an aluminum oxide filled column (activity IV, 45 g) while using as solvent medium, respectively that of its mixture with 2% ethanol as an eluent medium.

The unified obtained fractions, which include the less polar material I, were evaporated and the material obtained was purified by means of crystallization from from ethanol, and in the same way the unified fractions containing the more polar isoergoline-II-yl compound was treated. Material I melted at 203° to about 204°C (decomposition), ($\alpha/D^{20} = + 30°$ /c = 1.0, pyridine); the isomer isoergoline-II-yl compound melted at 208° to 210°C (decomposition), ($\alpha/D^{20} = + 80°$ /c = 0.45, pyridine).

The hydrogen maleate salt of material I was prepared from equivalent amounts of both components in ethanol. Fp. 190° to 191° C with decomposition (ethanol).

EXAMPLE 2

1.0 g D-dihydroisolysergic acid-I-hydrazide was converted in a known manner (l.c.) into the corresponding acid azide via the azide hydrochloride, from which in an aqueous medium the base was volatilized. From the alkaline aqueous medium the azide was taken up in 600 ml benzene; the azide solution was dried by passing it through a short molecular sieve column and was boiled for 10 minutes under reflux meanwhile keeping it free from the moisture in the surrounding atmosphere and under a nitrogen atmosphere. To the thus obtained isocyanate solution cooled to about 40°C, there was added a solution of 1.3 g diethyl-amine in 20 ml benzene; the reaction mixture was boiled for five minutes under reflux and under the same conditions as used for the production of the isocyanates. After the thus obtained product was allowed to stand for 20 hours at 20°C, the volatile ingredients were distilled off under the vacuum of a water pump and the crude product was purified by chromatographic aluminum oxide in a packed column (activity IV, 50 g) by using chloroform and its mixture with 2% ethanol as an eluent medium. The chromatographic process was followed simultaneously by means of paper-chromatography using the systems formamide-ammonium formate as stationary phase and chloroform as a mobile phase. The compound was identified on the basis of its fluorescence in the ultraviolet light by prior illumination with sunlight. The combined fractions contain already a very pure material I and were evaporated and the residue was re-crystallized from ethanol. The material obtained melts at 202° to 204°C (decomposition), ($\alpha$ /D$^{20}$ = + 29° /c = 0.45 pyridine). The corresponding hydrogen maleate salt was obtained as set forth in Example 1 above. Fp. 190° to 191°C with decomposition (ethanol).

What is claimed is:
1. N-(D-6-methyl-8-isoergoline-I-yl)-N,', N'-diethylurea of the formula

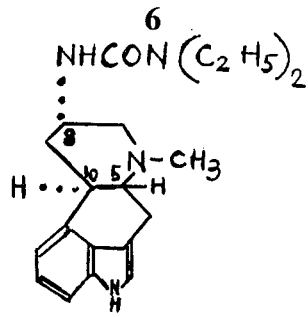

and its hydrogen maleate and tartrate salts

2. A salt according to claim 1 which is the hydrogen maleate salt of N-(D-6-methyl-8-isoergoline-I-yl)-N', N'-diethylurea.

3. A salt according to claim 1 which is the tartrate salt of N-(D-6-methyl-8-isoergoline-I-yl)-N', N'-diethylurea.

* * * * *